US009851285B2

(12) United States Patent
Bahorich et al.

(10) Patent No.: US 9,851,285 B2
(45) Date of Patent: Dec. 26, 2017

(54) DIGITAL DENSITOMETER AND FUEL GAUGING SYSTEM

(71) Applicant: Eaton Corporation, Cleveland, OH (US)

(72) Inventors: Phillip Andrew Bahorich, Laguna Hills, CA (US); Nalin Joshi, Playa Del Rey, CA (US)

(73) Assignee: Eaton Corporation, Cleveland, OH (US)

( * ) Notice: Subject to any disclaimer, the term of this patent is extended or adjusted under 35 U.S.C. 154(b) by 335 days.

(21) Appl. No.: 14/386,442

(22) PCT Filed: Mar. 21, 2013

(86) PCT No.: PCT/US2013/033349
§ 371 (c)(1),
(2) Date: Sep. 19, 2014

(87) PCT Pub. No.: WO2013/142717
PCT Pub. Date: Sep. 26, 2013

(65) Prior Publication Data
US 2015/0053004 A1 Feb. 26, 2015

Related U.S. Application Data

(60) Provisional application No. 61/613,762, filed on Mar. 21, 2012, provisional application No. 61/791,120, filed on Mar. 15, 2013.

(51) Int. Cl.
*G01N 9/00* (2006.01)
*G01N 33/22* (2006.01)
*G01N 9/36* (2006.01)

(52) U.S. Cl.
CPC ............... *G01N 9/36* (2013.01); *G01N 9/002* (2013.01); *G01N 33/22* (2013.01); *G01N 2009/006* (2013.01)

(58) Field of Classification Search
CPC .......... G01N 9/36; G01N 9/002; G01N 33/22; G01N 2009/006
(Continued)

(56) References Cited

U.S. PATENT DOCUMENTS 4,010,637 A * 3/1977 Harwell .............. G01P 15/0891
700/279
4,215,566 A 8/1980 Ghahramani
(Continued)

FOREIGN PATENT DOCUMENTS

CN 2545597 Y 4/2003
DE 19517135 * 12/1995

OTHER PUBLICATIONS

Philips Semiconductors, The I (square)-C_bus and how to use it, Apr. 1995.*
(Continued)

*Primary Examiner* — J M Saint Surin
(74) *Attorney, Agent, or Firm* — Fishman Stewart PLLC

(57) ABSTRACT

A digital densitometer for a fluid gauging system includes a frequency detection device configured to be disposed within a fluid tank, wherein a frequency detected by the frequency detection device is indicative of a density of a fluid within the fluid tank, frequency detection circuitry configured to obtain the frequency from the frequency detection device and output the frequency in a digital form, and an interface for digital communication with an electronic controller, the digital communication comprising transmission of the digital form of the frequency for the electronic controller.

19 Claims, 3 Drawing Sheets

(58) Field of Classification Search
USPC .......................................................... 73/579
See application file for complete search history.

(56) References Cited

U.S. PATENT DOCUMENTS

| | | | |
|---|---|---|---|
| 4,362,048 A | 12/1982 | Agar et al. | |
| 4,429,564 A | 2/1984 | Ikeda et al. | |
| 4,495,818 A | 1/1985 | Ikeda et al. | |
| 4,546,641 A | 10/1985 | Nguyen | |
| 4,802,360 A | 2/1989 | Maier | |
| 4,996,656 A * | 2/1991 | Hedrick | G01N 9/002 702/50 |
| 5,513,527 A * | 5/1996 | Griffiths | G01F 23/0069 340/945 |
| 5,533,381 A * | 7/1996 | Seale | G01F 11/086 73/19.03 |
| 5,602,333 A * | 2/1997 | Larrabee | G01F 23/26 324/681 |
| 6,389,891 B1 | 5/2002 | D'Angelico et al. | |
| 6,873,916 B2 * | 3/2005 | Kolosov | G01N 29/036 702/25 |
| 7,225,671 B2 * | 6/2007 | Atkinson | G01F 23/0076 73/149 |
| 8,281,655 B2 | 10/2012 | Bahorich et al. | |
| 2002/0184940 A1 | 12/2002 | Storm, Jr. et al. | |
| 2004/0200259 A1 | 10/2004 | Mattar | |
| 2006/0031030 A1 | 2/2006 | Bennett et al. | |
| 2009/0205411 A1 | 8/2009 | Müeller | |
| 2010/0251816 A1 * | 10/2010 | Bahorich | G01F 23/266 73/304 C |
| 2010/0292935 A1 | 11/2010 | Wakamatsu et al. | |
| 2012/0310579 A1 * | 12/2012 | Yan | G01N 9/002 702/100 |
| 2013/0180330 A1 * | 7/2013 | Gao | G01N 9/32 73/32 A |

OTHER PUBLICATIONS

European Patent Office; International Search Report and Written Opinion issued in corresponding International Patent Application No. PCT/US2013/033349, dated Oct. 15, 2013.
Article—Technology of Electronics Basis (AV), Jianying Liu, Beijing: Weapon Industry Publishing House, pp. 301-305, Jul. 2006.
Article—Design of Cylinder Shell Resonant Liquid Density Sensor, Yuming Fan, etc., Nanotechnology and Precision engineering, vol. 5, No. 2, pp. 134-138.
English Translation of Fourth Chinese Office Action, Application No. 2013800151876, dated Aug. 9, 2017.
Fourth Chinese Office Action, Application No. 2013800151876, dated Aug. 9, 2017.

* cited by examiner

DIGITAL DENSITOMETER AND FUEL GAUGING SYSTEM

CROSS-REFERENCE TO RELATED APPLICATIONS

This application is a national stage filing based upon International PCT Application No. PCT/US2013/033349, with an international filing date of Mar. 21, 2013, which claims the benefit of the filing date of U.S. provisional application No. 61/613,762, filed Mar. 21, 2012, and U.S. provisional application No. 61/791,120, filed Mar. 15, 2013, the entire disclosures of which are hereby incorporated by reference.

BACKGROUND a. Technical Field

This disclosure relates generally to fluid gauging systems and methods, including fuel-gauging systems and methods for determining the density of fuel associated with a fuel tank, such as an aircraft fuel tank.

b. Background Art

It is common to determine or estimate the density of fuel in an aircraft fuel tank in order to, among other things, determine the total fuel mass on board an airplane. With 14 C.F.R. Part 25 airplanes, the fuel quantity may be displayed in terms of mass, rather than volume, as the fuel mass does not change with temperature, and the amount of usable energy in the tanks is proportional to the mass of the fuel in the tank. Because densitometers have been traditionally expensive, heavy, and sometimes unreliable compared to other gauging components inside a fuel tank, some aircraft fuel quantity gauging systems may simply infer the density of the fuel density based on a fuel dielectric constant and/or fuel temperature. In some systems without densitometers, density determination can be the largest source of fuel gauging error.

Moreover, some conventional densitometers, which measure density as a function of the resonant frequency of a structure in contact with the fuel, include a vibrating spool. Vibrating spool type densitometers have been adopted for use in the majority of 14 C.F.R. Part 25 transports over 150 passengers. Operation of such vibrating spools and corresponding density calculations from the resulting data can be made.

It is noted that vibrating spool densitometers were initially developed for ground based petroleum applications, and were subsequently adopted for aircraft fuel gauging. Vibrating spool densitometers for aircraft are described in U.S. Pat. Nos. 4,802,360; 4,546,641; 4,495,818; and 4,215,566, all of which are hereby incorporated by reference as though fully set forth herein.

Consequently, it can be desirable to provide a highly accurate fuel quantity gauging system that can, inter alia, measure the fuel density and improve gauging accuracy.

BRIEF SUMMARY

An embodiment of a digital densitometer for a fluid gauging system may include a frequency detection device configured to be disposed within a fluid tank, wherein a frequency detected by the frequency detection device is indicative of a density of a fluid within the fluid tank, frequency detection circuitry configured to obtain the frequency from the frequency detection device, an analog-to-digital converter configured to convert the frequency into a digital form, and an interface for digital communication with an electronic controller, the digital communication comprising transmission of the digital form of the frequency for the electronic controller.

An embodiment of a hybrid digital densitometer for a fluid gauging system may comprise a frequency detection device disposed within a fluid tank, wherein a frequency detected by the frequency detection device is indicative of a density of a fluid within the fluid tank, a computer-readable memory configured to store a density calibration coefficient respective of the frequency detection device, an interface for communication with an electronic controller, the communication comprising the density calibration coefficient and the frequency, and a switch configured to selectively electrically couple the interface with the frequency detection device or with the computer-readable memory.

An embodiment of a digital densitometer system may comprise a frequency detection device disposed within a fluid tank, wherein a frequency detected by the frequency detection device is indicative of a density of a fluid within the fluid tank, frequency detection circuitry configured to obtain the frequency from the frequency detection device, an analog-to-digital converter configured to convert the frequency into a digital form, and an electronic controller, disposed outside of the fluid tank, configured to receive the frequency in the digital form and to determine a density of fluid within the fluid tank according to the frequency.

The foregoing and other aspects, features, details, utilities, and advantages of the present disclosure will be apparent from reading the following description and claims, and from reviewing the accompanying drawings.

BRIEF DESCRIPTION OF THE DRAWINGS

The accompanying drawings, which are included to provide a further understanding of the invention and are incorporated in and constitute a part of this specification, illustrate embodiments of the invention and, together with the detailed description, serve to explain aspects and features of the inventive concepts. In the drawings.

DETAILED DESCRIPTION

Reference will now be made in detail to embodiments of the present disclosure, examples of which are described herein and illustrated in the accompanying drawings. While the invention will be described in conjunction with embodiments, it will be understood that they are not intended to limit the present disclosure to these embodiments. On the contrary, the present disclosure is intended to cover alternatives, modifications and equivalents, which may be included within the spirit and scope of the present disclosure.

The included drawing figures generally illustrate two embodiments of an improved fluid gauging system. More specifically, and without limitation, FIGS. 1 and 2 generally illustrate embodiments of a digital densitometer (which may be referred to as a "pure" digital densitometer), and FIG. 3 generally illustrates a digital densitometer with remote drive (which may be referred to as a "hybrid" digital densitometer). Although the embodiments may be discussed in the context of aircraft fuel gauging, the disclosure is for illustration and explanation purposes, and should not be construed as limiting in nature. It will be appreciated by those of skill in the art that aspects of the embodiments disclosed herein may have application to many liquid gauging applications in which it is desirable to determine parameters associated with a fluid in a container or tank.

Figure 1:
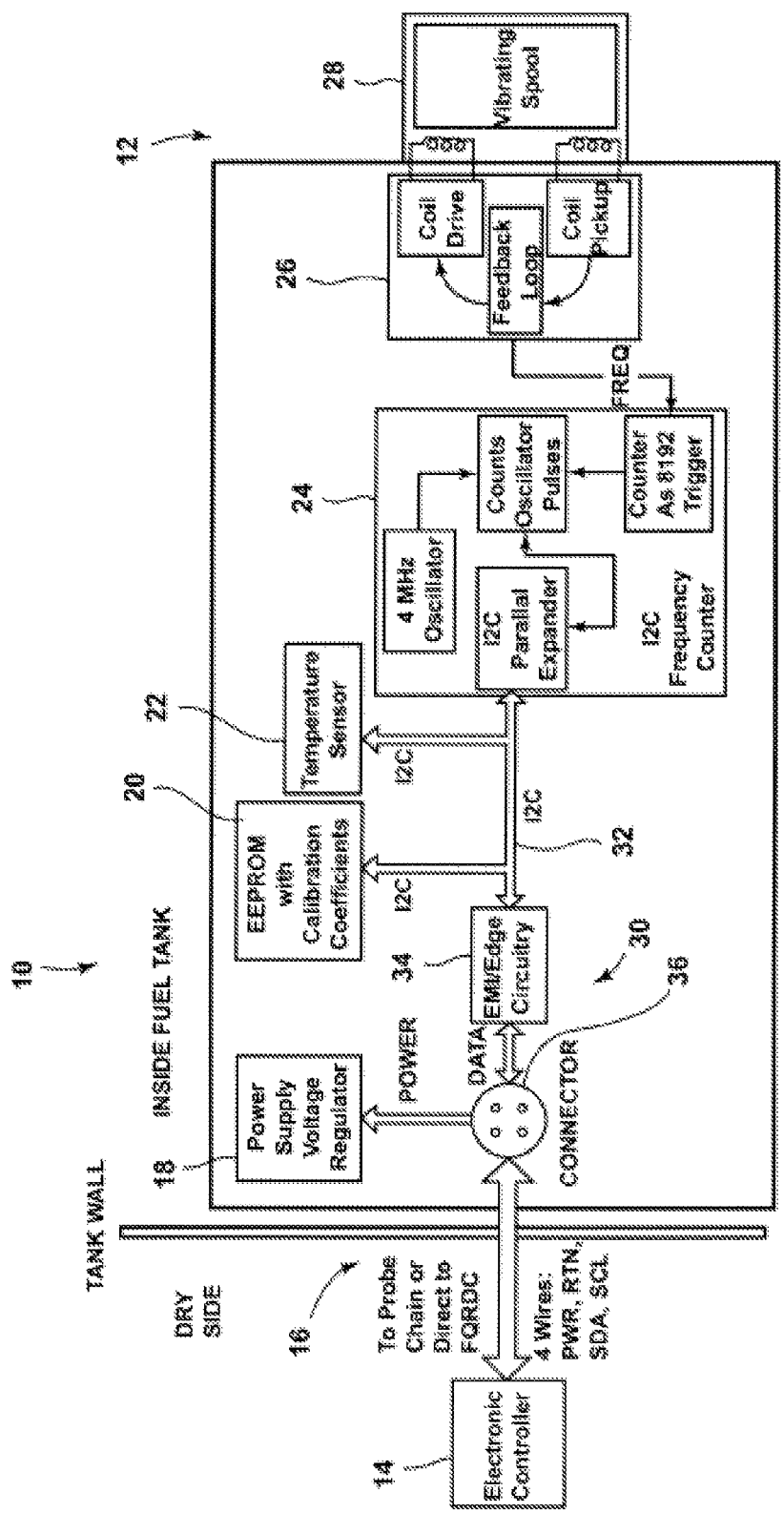
FIG. 1 generally illustrates a block diagram of an embodiment of a fuel gauging system with a digital densitometer.

FIG. 1 generally illustrates a digital densitometer system 10 including an embodiment of a pure digital densitometer 12 disposed within a fuel tank. The digital densitometer 12 is coupled with an exterior electronic controller 14 (e.g., a computer or programmable logic controller) disposed outside the tank through an electronic communication interface 16. The digital densitometer 12 may include, in an embodiment, a power supply voltage regulator 18, a non-volatile computer-readable memory 20, a temperature sensor 22, frequency detection circuitry 23 comprising a frequency counter 24 and drive and monitoring circuitry 26, and a frequency detection device 28.

The frequency detection device 28 may include or may be coupled with a structure configured to vibrate in fluid. The resonant frequency of the structure, which may correlate with or otherwise be associated with the density of the fluid in which the structure is disposed, may be determined and monitored to determine the density of the fluid. The frequency detection device 28 may include, in an embodiment, a vibrating spool. In other embodiments, the frequency detection device 28 may include other forms of densitometers that involve frequency readings including, without limitation, vibrating disk and tuning fork type densitometers. The densitometer 12 (and the other components described herein) may be adapted to or configured for any type of fluid tank (e.g., fuel, oil, hydraulic, water, etc.) in any type of vehicle (aircraft, rocket, ground vehicles, etc.), or even ground/stationary storage tanks of any type.

The frequency detection circuitry 23 may be similar to that provided in connection with conventional densitometers. As known, the drive and monitoring circuitry 26 may drive the frequency detection device 28 (i.e., cause one or more components or structures of the frequency detection device to vibrate) and may monitor the frequency detection device 28 to generate an analog signal indicative of the vibrating frequency of the frequency detection device 28. The drive and monitoring circuitry 26 may be similar to that of conventional densitometers, and may be similar to that shown and described in connection with U.S. Pat. Nos. 4,802,360, referenced above, and/or 4,996,656, which is hereby incorporated by reference as though fully set forth herein, and both of which address driving a spool over long wire lengths. The frequency counter 24 may receive this analog signal and output a digital signal indicative of the frequency detected by the frequency detection device 28. The frequency counter 24 may, in an embodiment, count the pulses of the analog signal with reference to a clock (i.e., the 4 MHz Oscillator shown in FIG. 1) and thereby determine a frequency of the frequency detection device 28.

The frequency counter 24 may output the digital signal over an internal communication interface 30 that may include a digital data bus (e.g., an I²C bus) 32, EMI/edge circuitry 34, and a connector 36. The connector 36 may provide, in an embodiment, a 4-pin (i.e., 4-wire) connection with the communication interface 16.

The memory 20 may be or may include an electrically erasable programmable read-only memory (EEPROM) or other known memory type. The memory 20 may be configured to store calibration coefficients respective of the frequency detection device 28, a configuration identifier respective of the frequency detection device 28, and/or other data, all of which data may be read from the memory 20 over the digital data bus 32 by the electronic controller 14.

The temperature sensor 22 may be provided on an independent integrated circuit (IC), in an embodiment—i.e., may be a dedicated temperature sensor 22. The temperature sensor 22 may comprise one or more sensors or other components known in the art. The temperature sensor 22, like the memory 20, may be configured for communication over the digital data bus 32 with the electronic controller 14.

The digital data bus 32 may comprise a modified digital bus (e.g., an I²C bus) similar to a digital probe bus, and further may employ a similar four wire interface for reading from the memory 20, reading from the temperature sensor 22, and for communication of a frequency (in digital form) respective of the frequency detection device 28. The digital data bus 32 may be combined with a digital probe bus, in an embodiment. For such a combination, the power supply may be modified, since the drive and monitoring circuitry 26 may draw 12 mA at 12 volts, while the digital probe power may be 4.75 volts with a current limit of 12 mA. With embodiments of the disclosure, the densitometer 12 does not require an on-board microprocessor, programmable logic device (PLD), field-programmable gate array (FPGA), or other programmable hardware inside the fluid tank. Further, and in contrast to a digital probe, the densitometer 12 does not require an internal multiplexer to provide digital addressing. Additional disclosure concerning common or similar relevant components of a system for use in a similar environments, including without limitation transformation of signals to digital form and communications over a digital bus, such as a probe bus, are included in U.S. patent application Ser. No. 12/418,172 (issued as U.S. Pat. No. 8,281,655), filed Apr. 3, 2009, which is hereby incorporated by reference as though fully set forth herein.

In an embodiment, the memory 20, the temperature sensor 22, and the frequency, detection circuitry 23, as applicable, all may have uniquely assignable addresses (e.g., I²C addresses) or sub addresses, which is also unique from any digital probe. Accordingly, devices and systems according to the present disclosure may not require a multiplexer, as with conventional digital probes.

The electronic controller 14 may be electrically coupled with and configured to provide power to and to communicate with the pure digital densitometer 12 over the communication interface 16. The electronic controller 14 may be configured to receive data such as, for example and without limitation, the frequency (in digital form) of the frequency detection device 28, calibration parameters respective of the frequency detection device 28 (e.g., stored in the memory 20), and a temperature from the temperature sensor 22. According to the frequency and calibration parameters, the electronic controller 14 may determine the density of the fluid in the tank.

The pure digital densitometer 12 may simplify the interface 16 with the electronic controller 14 by only requiring a four (4) wire connection as compared with known densitometers, which may require up to eight (8) wires for power and analog communication between a controller and a densitometer. In addition, the pure digital densitometer 12 may not require shielding of the tank harness, as the interface 16 may operate sufficiently without shielding.

Figure 2:
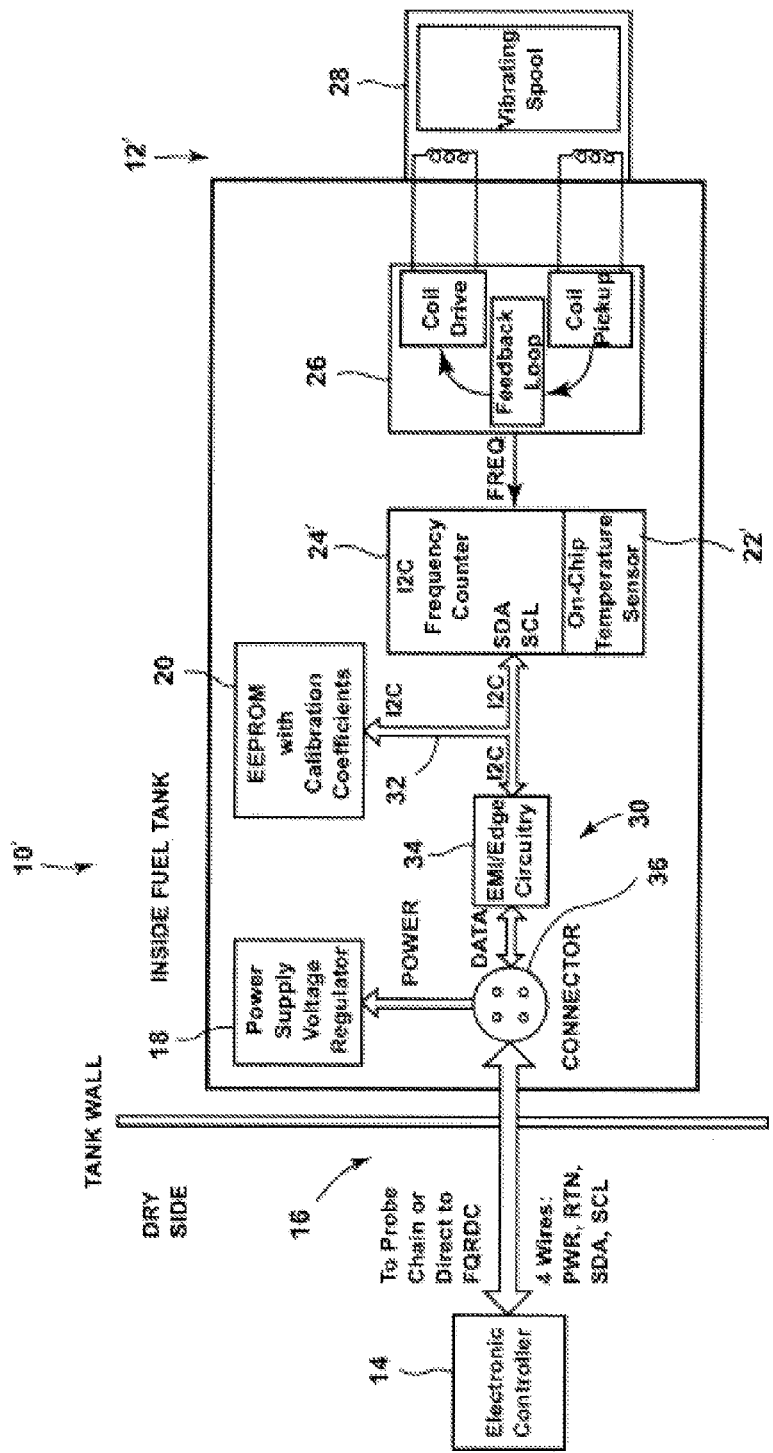
FIG. 2 generally illustrates a block diagram of another embodiment of a fuel gauging system with a digital densitometer.

FIG. 2 illustrates a digital densitometer system 10' including an alternate embodiment of a pure digital densitometer 12'. The densitometer 12' of FIG. 2 is substantially the same as (and presents substantially the same advantages as), the densitometer 12 of FIG. 1, except the densitometer 12' of FIG. 2 includes a temperature sensor 22' that is integrated with an frequency counter 24'—i.e., the frequency counter 24' and temperature sensor 22' may be provided on the same IC.

Figure 3:
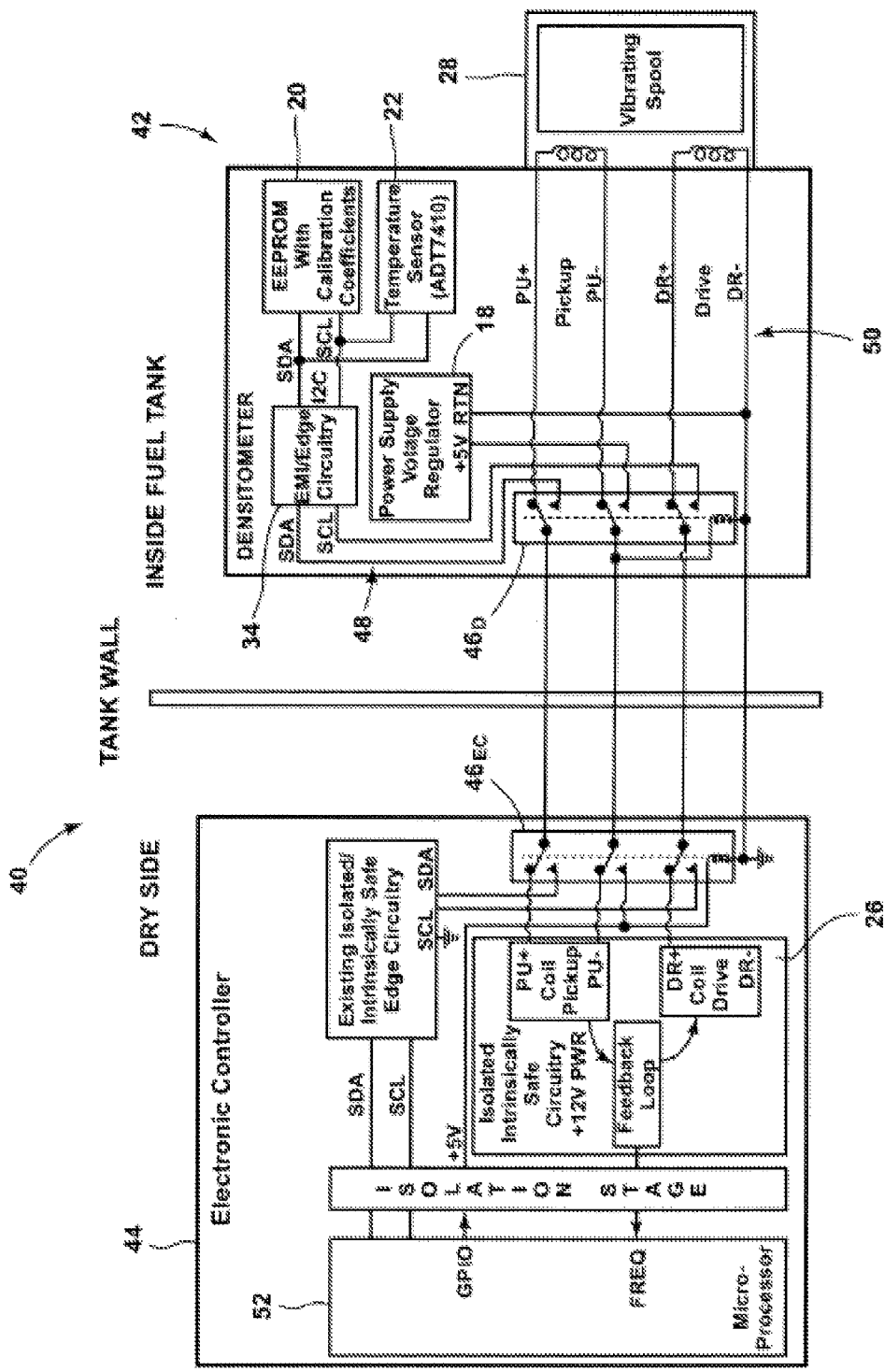
FIG. 3 generally illustrates a block diagram of another embodiment of a fuel gauging system with a digital densitometer.

A digital densitometer system 40 including an embodiment of a hybrid densitometer 42 is generally illustrated in FIG. 3. The illustrated hybrid densitometer 42, as compared with the pure digital densitometers 12, 12' disclosed herein, removes from the fluid tank the circuitry responsible for driving and monitoring the frequency detection device 28 and for counting, determining, and/or digitizing the resultant frequency. Accordingly, the hybrid densitometer 42 may be configured to be disposed within the fluid tank and may include a frequency detection device 28, a non-volatile computer-readable memory 20, a temperature sensor 22, a power supply voltage regulator 18, and EMI/edge circuitry 34. The hybrid densitometer 42 may be electrically coupled with an electronic controller 44 disposed outside of the fluid tank.

The frequency detection device 28, temperature sensor 22, and memory 20 may comprise components and functionality substantially as described above with respect to the pure digital densitometers 12, 12'. In the hybrid digital densitometer 42, the frequency detection device 28, temperature sensor 22, and memory 20 may be selectively electrically coupled with the electronic controller 44 through complementary switches $46_{EC}$, $46_D$ respectively disposed in the electronic controller 44 and the densitometer 42 (and which may be collectively or individually referred to simply as switches 46). The switches 46 may comprise, for example, solid-state switches. The switches 46 may, in a first state, electrically couple the memory 20 and temperature sensor 22 with the electronic controller 44 via a digital data bus 48 and, in a second state, electrically couple the frequency detection device 28 with the electronic controller 44 via an analog connection 50.

The electronic controller 44 may include, in an embodiment, one of the switches $46_{EC}$ mentioned above, drive and monitoring circuitry 26, and a micro-processor 52. The drive and monitoring circuitry 26 may include components and functionality substantially as described above.

The micro-processor 52 may be configured to receive, in an embodiment, an analog signal from the drive and monitoring circuitry 26 indicative of the frequency of the frequency detection device 28 as well as digital signals including communications transmitted over the digital data bus 48. The micro-processor 52 may, in an embodiment, include a frequency counter to determine a frequency based on the analog signal from the drive and monitoring circuitry 26, or a frequency counter may be disposed between the drive and monitoring circuitry 26 and the micro-processor 52. The micro-processor 52 may include programming and functionality substantially as described above with respect to the electronic controller 14 of FIG. 1 and FIG. 2.

With continued reference to FIG. 3, in an embodiment, the switches 46 may allow the electronic controller 44 to either drive/monitor the frequency of the frequency detection device 28 or read the temperature and calibration coefficients, for example, depending on the switch positions as selected by the electronic controller 44 at the GPIO port. With the switches 46 in a first state, as shown in FIG. 3, the electronic controller 44 may read the memory 20 over the digital data bus 48 on power up and determine, for example, if it is a digital densitometer along with calibration parameters, and also read the temperature from the temperature sensor 22. If it is a digital densitometer, the electronic controller 44 may energize or activate the switches 46 to a second state, so that the drive and the monitoring circuitry 26 can be used to directly determine the frequency of the frequency detection device 28.

Embodiments of densitometers 12, 12', 42 associated with the disclosed systems 10, 10', 40 may provide numerous advantageous features. For example, the densitometers disclosed herein may provide a digital signal output using no microprocessor or custom coded micro-components (such as a PLD, FPGA, or Application Specific Integrated Circuit (ASIC)), may provide for digital storage of calibration data on the densitometer(s), such that the data may be read digitally by an interfacing electronic controller to then calculate fluid density, and may provide digital temperature data at the densitometer(s), such that the data may be read digitally by the interfacing electronic controller. The densitometers and systems disclosed herein may also advantageously be digitally addressed from an electronic controller at a different/remote location, provide digital calibration and/or configuration recognition to an electronic controller at a different/remote location, and share a common set of wires in the fuel tank with a digital probe (at least with respect to disclosed "pure" densitometers). Such a digital probe may be found in U.S. Pat. No. 8,281,655, referenced above.

A number of potential benefits may be provided by embodiments according to the present disclosure. For example, simplified harnesses may be provided in an airplane, for example, including in the fuel tank, between the densitometer and electronic controller (e.g., fuel gauging computer/PLC). Typical conventional densitometers use 8 shielded wires to read the densitometer (2 to drive the sensor head, 2 to monitor the sensor head, and 4 to read the custom chosen resistors which represent calibration coefficients K0 and K2 unique to each sensor produced). Embodiments of the disclosed densitometers may use just 4 unshielded wires in the fuel tank (similar to a digital probe). However, it is noted that with a "hybrid" densitometer, such as illustrated in FIG. 3, it may be necessary or desirable to shield the 4 wires, depending on the needs and desired results (which may be in part determined by EMI testing).

An additional advantage that may be provided by embodiments according to the present disclosure is temperature reading at the densitometer. Conventional densitometers commonly lack temperature sensors. Adding such sensors would typically add two more wires to the harness. With the disclosed embodiments, the use of a digital data bus permits the reading of the temperature at the densitometer, for example, through a temperature sensor built into an analog-to-digital converter circuit, or through a dedicated I²C temperature sensor (such as the ADT7410). The inclusion of a temperature sensor allows the temperature at the densitometer to be compared to the temperature at various locations in the tank via separate temperature sensors or as inherent to a digital probe (e.g., Digital Probe™) system. Temperature comparisons can allow the density measured to be adjusted at various locations in the tank, which can improve the accuracy of fuel quantity calculations.

An additional advantage that may be provided by embodiments according to the present disclosure is improved digital interfacing. Utilizing a digital interface (such as I²C) and addressing allows densitometers to share circuitry inside the electronic controller with digital probes. This can, among other things, reduce complexity in the computer (e.g., in both pure digital and hybrid digital densitometer embodiments) and allows bus wires (e.g., I²C bus wires) to be shared with digital probes (e.g., in pure digital densitometer embodiments).

An additional advantage that may be provided by embodiments according to the present disclosure is facilitation of functional testing at installation. It has been observed that vibrating spools may not consistently oscillate in air. Some units come off the production line randomly having the ability to do so, while others do not. Because the heads may not reliably vibrate in air (air point), it can be challenging to test that a densitometer installation is correct, particularly that harnessing between the densitometer and electronic controller is properly installed (e.g., that the densitometer is receiving power from the electronic controller and can communicate back). Embodiments of the disclosed densitometer provide such an ability since digital communication may take place regardless of whether the spool has reached an oscillation point or not.

An additional advantage that may be provided by embodiments according to the present disclosure is electromagnetic interference (EMI) resistance. Digital interfaces, such as those disclosed, may be EMI resistant.

An additional advantage that may be provided by embodiments according to the present disclosure is simplified driving of signals. For example, with a pure digital densitometer embodiment, the inclusion of a digital interface can simplify and address the challenge of driving the densitometer over a long wire length.

An additional advantage that may be provided by embodiments according to the present disclosure is digital calibration coefficients. Vibration style densitometers sensor heads generally all require individual calibration to help ensure accuracy. The resulting calibration coefficients (e.g., K0 and K2) are generally passed to the processing electronics to determine fuel density. In an embodiment, resistors may be provided for the calibration coefficients as an alternative to the computer-readable memory disclosed herein. Such resistor-based calibration coefficients may be included according to the disclosure of U.S. Pat. No. 4,802,360, referenced above. The resistors may be individually chosen to represent the calibration coefficients and may be permanently mated to the frequency detection device to be read by an electronic controller. This generally requires additional dedicated wires in the harness before running between the computer and densitometer.

Although particular embodiments of the invention have been described in detail herein with reference to the accompanying drawings, it is to be understood that the invention is not limited to those particular embodiments, and that various changes and modifications may be effected therein by one skilled in the art without departing from the scope or spirit of the invention as defined in the appended claims.

What is claimed is:

1. A digital densitometer for a fluid gauging system, the densitometer comprising:
    a frequency detection device configured to be disposed within a fluid tank, wherein a frequency detected by the frequency detection device is indicative of a density of a fluid within the fluid tank;
    frequency detection circuitry configured to be disposed within the fluid tank and to obtain the frequency from the frequency detection device and to output the frequency in a digital form;
    a data bus having a temperature sensor integrated with a frequency counter is configured to count pulses of an analog signal with reference to a clock and determine a frequency of the frequency detection device, wherein the frequency detection circuitry is in communication with one or more additional components over the data bus, and the frequency detection circuitry is associated with a unique address on the data bus; and
    an interface for digital communication with an electronic controller, the digital communication comprising transmission of the digital form of the frequency for the electronic controller, calibration parameters of the frequency detection device, and a temperature from the temperature sensor.

2. The digital densitometer of claim 1, wherein the data bus is an I²C bus.

3. The digital densitometer of claim 1, wherein the temperature sensor comprises an integrated circuit that is separate from the frequency detection circuitry and the analog-to-digital converter.

4. The digital densitometer of claim 1, wherein the temperature sensor is integrated into the analog-to-digital converter.

5. The digital densitometer of claim 1, wherein the frequency detection device comprises a vibrating spool.

6. The digital densitometer of claim 1, wherein the frequency detection device comprises a vibrating disk.

7. The digital densitometer of claim 1, wherein the frequency detection device comprises a tuning fork.

8. The digital densitometer of claim 1, wherein the frequency detection device is configured to detect a resonant frequency of a structure in contact with the fluid in the fluid tank.

9. The digital densitometer of claim 1, wherein the interface comprises a four wire connector.

10. The digital densitometer of claim 1, further comprising a computer-readable memory configured to store a density calibration coefficient respective of the frequency detection device, wherein the digital communication further comprises transmission of the density calibration coefficient for the electronic controller.

11. The digital densitometer of claim 10, wherein the memory is configured to be disposed inside of the fluid tank.

12. A hybrid digital densitometer for a fluid gauging system, the densitometer comprising:
    a frequency detection device disposed within a fluid tank, wherein a frequency detected by the frequency detection device is indicative of a density of a fluid within the fluid tank;
    a computer-readable memory configured to store a density calibration coefficient respective of the frequency detection device;
    an interface for communication with an electronic controller over a data bus having a temperature sensor integrated with a frequency counter is configured to count pulses of an analog signal with reference to a clock and determine a frequency of the frequency detection device, wherein the memory is associated with a unique address on the data bus, the communication comprising the density calibration coefficient and the frequency; and
    a switch configured to selectively electrically couple the interface via the data bus with the frequency detection device or with the computer-readable memory.

13. The hybrid digital densitometer of claim 12, further comprising a temperature sensor, wherein the solid state switch is configured to selectively electrically couple the interface with the frequency detection device or with the computer readable memory and the temperature sensor.

14. The hybrid digital densitometer of claim 12, wherein the densitometer is configured to be disposed inside of the fluid tank.

15. The hybrid digital densitometer of claim 12, wherein the interface is configured for electrical coupling over the data bus with frequency detection circuitry, disposed outside of the fluid tank, configured to obtain the frequency from the frequency detection device, and an analog-to-digital converter, disposed outside of the fluid tank, configured to convert the frequency into a digital form.

16. A digital densitometer system, comprising:
   a frequency detection device disposed within a fluid tank, wherein a frequency detected by the frequency detection device is indicative of a density of a fluid within the fluid tank;
   frequency detection circuitry configured to obtain the frequency from the frequency detection device output the frequency in a digital form;
   an electronic controller, disposed outside of the fluid tank, configured to receive the frequency and to determine a density of fluid within the fluid tank according to the frequency; and
   a data bus having a temperature sensor integrated with a frequency counter is configured to count pulses of an analog signal with reference to a clock and determine a frequency of the frequency detection device, wherein the frequency detection circuitry is in communication with one or more additional components over the data bus, and the frequency detection circuitry is associated with a unique address on the data bus.

17. The digital densitometer system of claim 16, wherein the frequency detection circuitry is disposed within the fluid tank.

18. The digital densitometer system of claim 16, further comprising a computer readable memory, disposed within the fuel tank, configured to store a density calibration coefficient respective of the frequency detection device.

19. The digital densitometer of claim 18, wherein the electronic controller is configured to determine a density of fluid within the fluid tank according to the frequency and according to the density calibration coefficient.

* * * * *